United States Patent [19]

Lieber et al.

[11] Patent Number: 5,313,967

[45] Date of Patent: May 24, 1994

[54] HELICAL GUIDEWIRE

[75] Inventors: Glen L. Lieber, Poway; Ronald J. Solar, San Diego; Erich H. Wolf, Vista; Mauricio L. Fugoso, Jr., Chula Vista, all of Calif.

[73] Assignee: Medtronic, Inc., Minneapolis, Minn.

[21] Appl. No.: 919,484

[22] Filed: Jul. 24, 1992

[51] Int. Cl.⁵ .............................................. A61M 25/00
[52] U.S. Cl. .................................... 128/772; 604/170; 606/194
[58] Field of Search ............... 604/95, 164, 167, 170, 604/267, 96; 128/657, 772; 606/192, 194

[56] References Cited

U.S. PATENT DOCUMENTS

| | | | |
|---|---|---|---|
| 3,732,858 | 5/1973 | Banko | 604/267 |
| 3,789,841 | 2/1974 | Antoshkiw | 128/2.05 R |
| 4,228,802 | 10/1980 | Trott | 604/267 |
| 4,345,602 | 8/1982 | Yoshimura et al. | 128/349 R |
| 4,474,174 | 10/1984 | Petruzzi | 128/4 |
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,719,924 | 1/1988 | Crittenden et al. | 128/772 |
| 4,721,117 | 1/1988 | Mar et al. | 128/772 |
| 4,763,647 | 8/1988 | Gambale | 128/657 |
| 4,811,743 | 3/1989 | Stevens | 128/772 |
| 4,827,941 | 5/1989 | Taylor et al. | 128/657 |
| 5,007,434 | 4/1991 | Doyle et al. | 128/772 |

Primary Examiner—John D. Yasko
Assistant Examiner—Anthony Gutowski
Attorney, Agent, or Firm—Dianne M. F. Plunkett; Harold R. Patton

[57] ABSTRACT

A torque-transmitting structure such as a guidewire or catheter is formed of a generally flat band or wire twisted so that its longitudinal edge generally forms a helix. This twisted helical portion may be attached to a proximal shaft, and a tip member may be attached to the distal end of the helical portion. In some embodiments, the device is made of a single piece of wire, and in some embodiments, a spring coil may cover the helical portion. Where the device is a fixed wire balloon catheter, the helical portion may be attached to a proximal shaft, and the balloon mounted on the helical twisted wire, a plastic sheath encasing the main shaft and wire up to the balloon for inflation of the balloon. The helical guidewire may also be used in an over-the-wire balloon catheter.

23 Claims, 4 Drawing Sheets

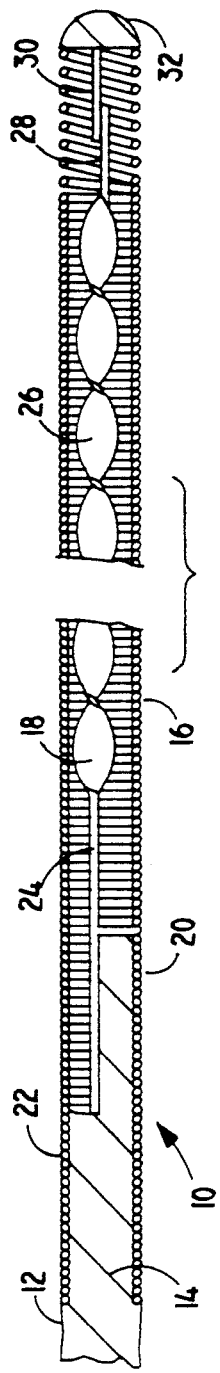
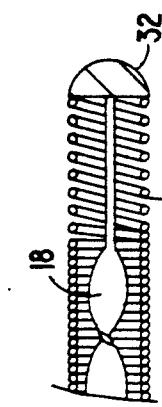
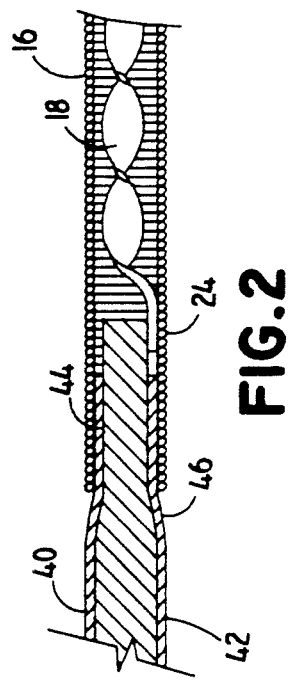
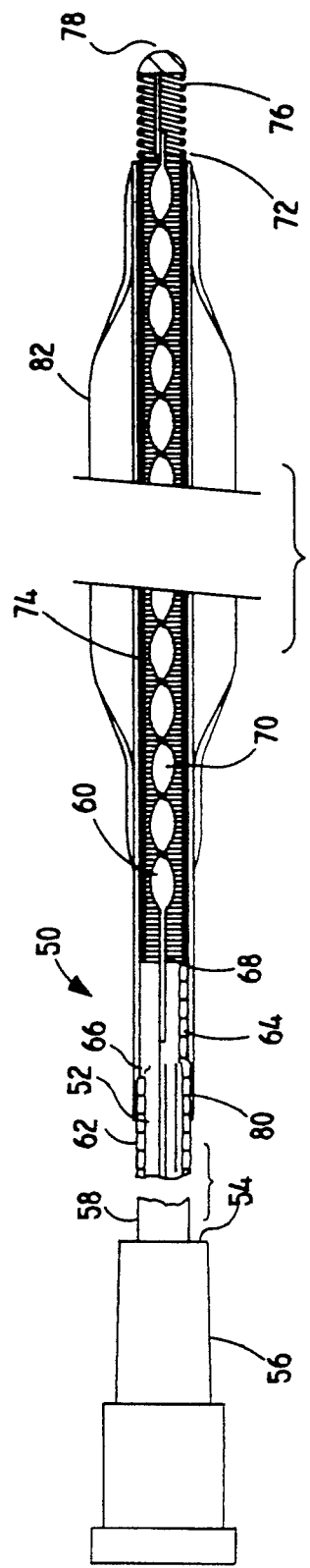

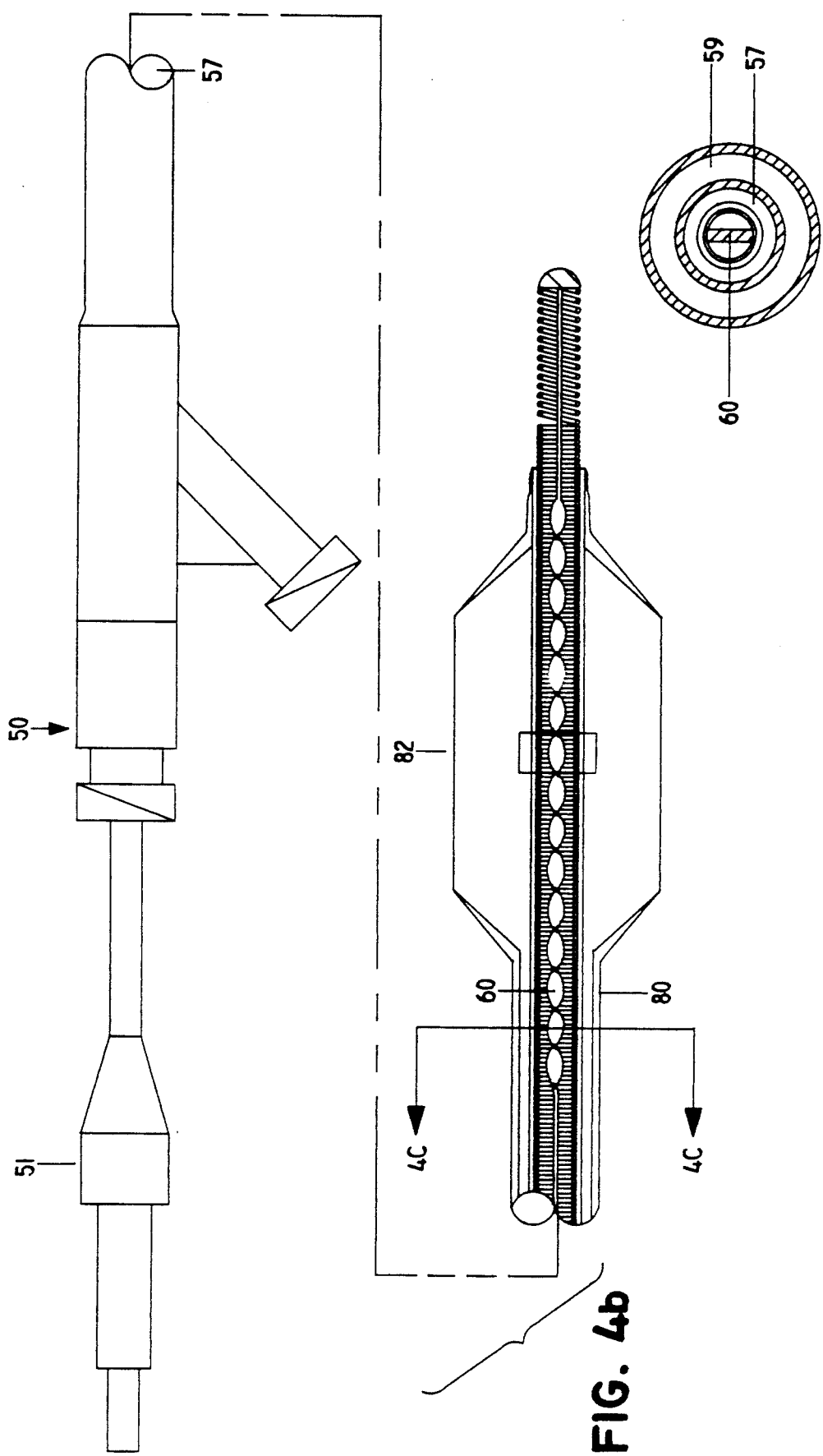

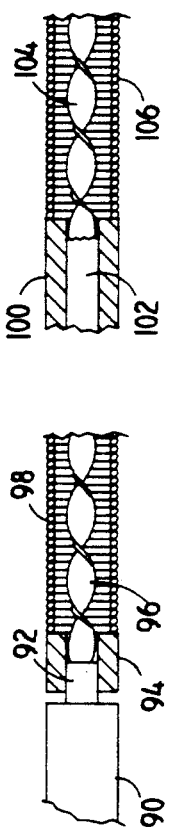
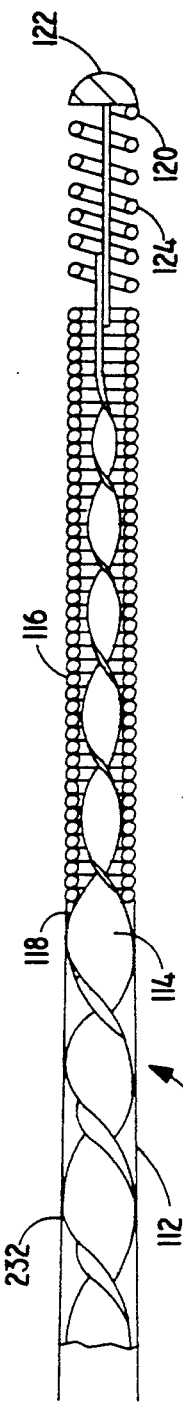
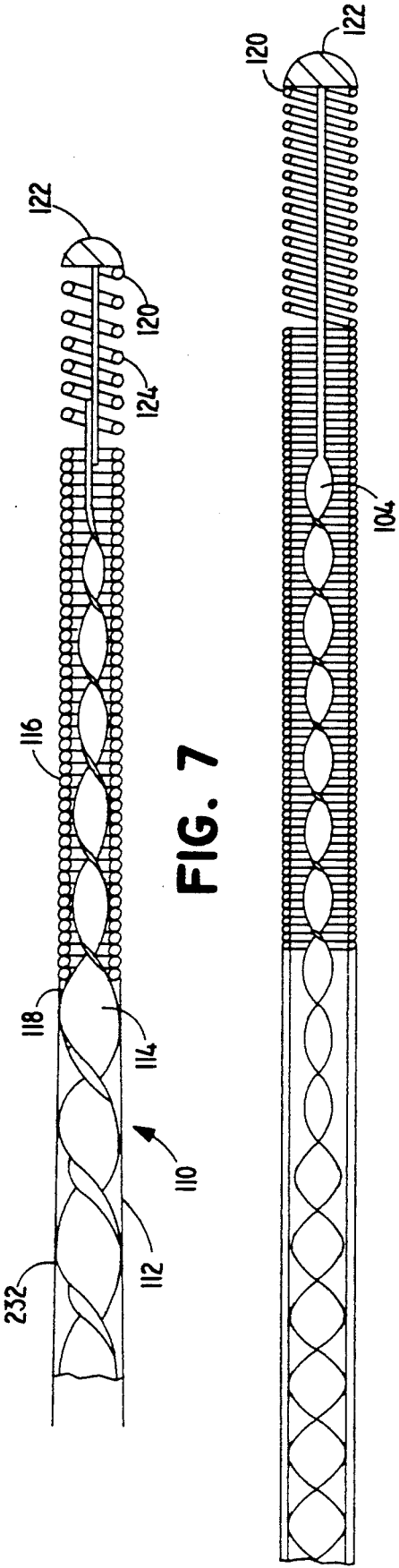
FIG. 5  FIG. 6  FIG. 7  FIG. 7a  FIG. 8

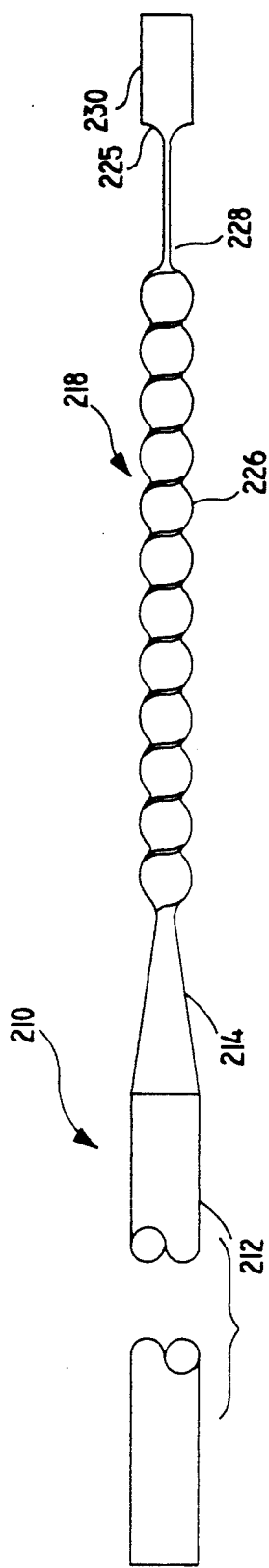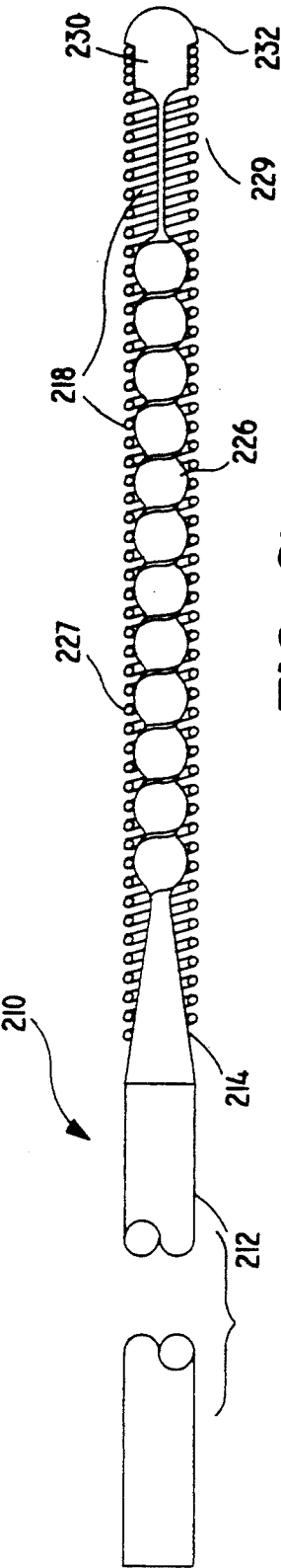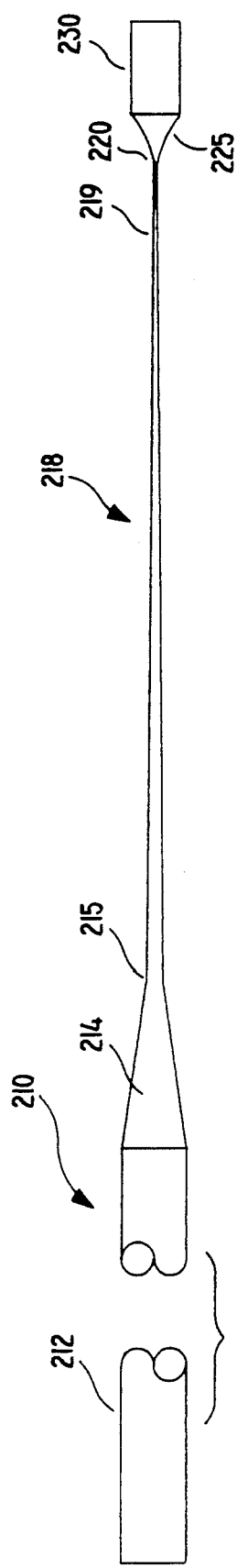

HELICAL GUIDEWIRE

BACKGROUND OF THE INVENTION

Field of the Invention

This invention relates to structures for insertion into body organs such as guidewires and catheters.

Background of the Invention

The design of medical devices for insertion into body organs has always involved trading off various performance characteristics in the design of a satisfactory implement. For some applications insertion requires a device which is stiff enough to be pushable and to transmit torque along the body of the device, while being flexible enough to go around bends.

For example, insertion of guidewires and catheters into arteries requires that the device follow a tortuous path through small arteries. For this, great flexibility is required.

On the other hand, in order to select branches within arteries, the device must be steered and turned. Therefore, torque must be transmitted. In order to overcome friction within the artery, the device must be sufficiently pushable.

It can be seen that these characteristics, while easily accomplished in a large device, may be mutually exclusive in a very small diameter device such as a catheter or guidewire for coronary arteries.

The flexibility of the tip section of such devices has been of particular interest. The common technique has been to surround a shaft with a flexible tip spring. For example, in U.S. Pat. No. 3,789,841 to Antoshkiw, a main wire is tapered, and a flexible spring is mounted over the wire. The same structure is later used in U.S. Pat. No. 4,545,390 to Leary.

The following patents, U.S. Pat. No. 4,474,174 to Petruzzi, U.S. Pat. No. 4,763,647 to Gambale, and U.S. Pat. No. 5,007,434 to Doyle disclose helically twisted wires used to accomplish various functions. U.S. Pat. No. 4,474,174 to Petruzzi discloses a surgical cutting tool in which the helically twisted flat ribbon is sized to slidingly fit within the lumen of a tubular member. The Petruzzi invention, however, structures the helical ribbon to accomplish back-and-forth motion via control wheel 42 and 42' as well as with structural rigidity and reduced longitudinal backlash as required by surgical tools. The Petruzzi control wire 60 helical structure is directed to providing a continuous fluid passageway. See column 8 line 25 and column 12 line 24. The helical structure is not directed to torquability as is applicant's.

In U.S. Pat. No. 4,763,647 to Gambale, an outer helically wound coil is mounted on the distal region of a guidewire and an inner helical coil is disposed within the first coil. The Gambale outer coil 16 and inner coil 22, however, are not ribbon wires twisted around the ribbon wire's longitudinal axis as in the applicants' invention. In Gambale, the coils are wound around the tapered shaft, 10. When the shaft tappers off, the coil spring center is hollow.

In U.S. Pat. No. 5,007,434 to Doyle, et al., the helical coil has a plurality of bends conforming to the bends in the shaft over which it extends thereby providing angular control of the tip attitude as opposed to a design directed to torquability as is applicant's.

This description of art is not intended to constitute an admission that any patent, publication or other information referred to is "prior art" with respect to this invention, unless specifically designated as such. In addition, this section should not be construed to mean that a search has been made or that no other pertinent information as defined in 37 C.F.R. § 1.56(a) exists.

The various attempts at tapering the shaft and shaping the spring have all had their benefits and faults as part of the design process. What is needed is a structure which provides the needed pushability and torque transmission in the tip area while being flexible and of low profile.

SUMMARY OF THE INVENTION

The present invention involves a torque-transmitting structure formed of a generally flat band twisted around its longitudinal axis. The longitudinal edges thus take a generally helical configuration so that the device is capable of transmitting torque while remaining flexible. The amount of twisting and/or the wire width may vary over the length of the wire. In one embodiment, the invention involves a guidewire having a shaft with a longitudinally-twisted wire attached to its distal end. A distal tip member is attached to a short piece of straight wire which is attached in turn to the distal end of the twisted wire. In another embodiment, the entire guidewire, including shaft, twisted helix and tip, is made of a unitary piece of metal. A spring coil may, in some embodiments, cover the helical twisted wire.

In another form of the invention, a catheter, usually of the fixed-wire type, includes a wire formed of a shaft twisted as above. In some embodiments of the catheter, the twisted helical flat wire of the present invention forms a distal shaft which is in turn attached to an untwisted main shaft which extends the remaining length of the catheter. A balloon is mounted over the twisted helical flat wire. A plastic sheath encases the main wire up to the balloon for inflation of the balloon. Other variations in the shaft are as described above.

Other embodiments comprise a single twisted band which is encased in plastic.

BRIEF DESCRIPTION OF THE DRAWINGS

FIG. 1 is a cross-section of a guidewire constructed according to the present invention.

FIG. 2 is a fragmentary cross-section of an alternative embodiment of the guidewire of FIG. 1.

FIG. 3 is a fragmentary cross-section of an alternative embodiment of the tip of the guidewire of FIG. 1.

FIG. 4a is a broken-away view of a fixed-wire balloon catheter embodiment of the present invention having a helical guidewire.

FIG. 4b is a broken-away view of an over-the-wire balloon catheter having a helical guidewire.

FIG. 4c is a cross-sectional view taken along line 4c–4c of FIG. 4b of an over-the-wire balloon catheter having a helical guidewire.

FIG. 5 is a fragmentary cross-section of an alternative embodiment of the guidewire of FIG. 1.

FIG. 6 is a fragmentary cross-section of an alternative embodiment of the guidewire of FIG. 1.

FIG. 7 is a fragmentary cross-section of an alternative embodiment with the distal portion shown in cross-section.

FIG. 7a is a fragmentary cross-section of an alternative embodiment of the tip of the guidewire of FIG. 7.

FIG. 8 is a fragmentary cross-section of an alternative embodiment of the guidewire of the present invention.

FIG. 9a is a cross-section of a unitary embodiment of the guidewire of the present invention.

FIG. 9b is a cross-section of a unitary guidewire in which the helical coil is surrounded by a spring coil.

FIG. 10 is a side elevation of a unitary guidewire of the present invention before helical twisting of the wire has occurred.

DESCRIPTION OF THE PREFERRED EMBODIMENTS

A guidewire 10 constructed according to the present invention is illustrated in FIG. 1. It is formed of a biocompatible metallic material, usually stainless steel or other metallic or polymer alloys. Guidewire 10 in this embodiment includes a main shaft 12 which is a solid core wire. One skilled in the art could select other types of main shafts, such as hollow tubes. In this embodiment, shaft 12 includes a section 14 of reduced diameter. Section 14 is preferably formed by grinding down shaft 12. A tip spring 16 is mounted on shaft 12 over region 14.

Wire 18 is attached to a distal tip 20 of shaft 12. In this embodiment, shelf 22 is formed in distal tip 20, preferably by grinding, to receive wire 18. Wire 18 is formed of flat stock, preferably 0.003 inches thick and 0.010 inches in width. It is understood by those skilled in the art that a larger or smaller wire design requires different dimensions. Wire 18 has a straight proximal section 24, helix or twisted section 26 and a straight distal section 28. Distal section 28 may be tapered from the helix 26 to a ground round wire. Sizes are listed as examples of this embodiment used in coronary arteries. Other sizes may be employed by those skilled in the art.

The helix or twisted section 26 is formed by rotating a flat wire 18 (or, for example, in FIG. 10, 218) about its longitudinal axis so that its edges generally form a helix. Other methods of making the twist, i.e., molding or grinding are possible. The resulting twisted wire is somewhat like a screw or auger. Unlike other coils formed from flat bands, the twist provides the device with axial pushability and torque transmission by minimizing the tendency to bend. In the embodiment illustrated in FIG. 1, a tip wire 30 is attached, preferably by brazing, to the straight distal section 28 of twisted wire 26. Those skilled in the art will recognize that where metals are concerned, attachment methods other than brazing are generally possible, as for example, welding. Tip wire 30 is, in turn, brazed to a tip member 32. Tip member 32 is also brazed to coil 16. Many other configurations of the tip area may be used as shown in the prior art.

Helix wire 18 has greatly improved pushability and torque transmission over prior art designs, relative to its flexibility. Unlike prior art devices in which similar design goals were accomplished by adjusting the bulk of the wire, this design accomplishes the design goals through novel construction.

An alternative embodiment of the connection of wire 18 to the shaft is illustrated in FIG. 2. In this embodiment, shaft 40 is constructed of a hollow tube, such as hypodermic needle tubing. Shaft 40 has a proximal section 42 of a first diameter and a distal portion 44 of a smaller diameter. The smaller diameter is reached by necking down tube 40 at 46. The proximal flat portion 24 of wire 18 is attached preferably by brazing to section 44 of shaft 40. Spring 16 is then mounted over section 24 and section 44.

An alternate embodiment of the tip area is illustrated in FIG. 3 where distal section 28 of wire 18 is attached directly to tip member 32. Distal section 28 may be tapered to round diameter.

FIG. 4a is an illustration of the use of the present invention in a catheter. Many of the parts of catheter 50 are conventional, and there are substitutes known to those skilled in the art. The illustrated embodiment includes a main body 52 with a proximal end 54 attached to fitting 56. Fitting 56 is for the attachment of inflation devices and other apparatus known in the prior art. Body 52 has a lumen 58.

Helix wire 60 is mounted on body 52. In this embodiment, body 52 has a proximal section 62 of a first diameter and a distal section 64 of second diameter, in this example, formed by necking down at 66. Helix wire 60 has as flat proximal section 68, helix portion 70 and a distal portion 72 which may be flat or ground to a taper. Proximal section 68 is attached, preferably by brazing, to section 64 of body 52. A tip spring 74 is attached over section 60, preferably by brazing.

As discussed above, in relation to the other embodiments, a tip wire 76 is mounted on section 72 preferably by brazing. In turn, wire 76 is brazed to tip member 78. Tip member 78 is also brazed to coil 74.

A plastic skin 80 is attached over shaft 52 and spring 74 in a conventional manner A balloon 82 is mounted on skin 80 in a conventional manner so that the interior balloon is open to lumen 58 for inflation. In this embodiment, the wire 60 operates to provide a torque transmitting body which is pushable while remaining flexible.

FIG. 4b and 4c illustrate an over-the-wire balloon catheter having a helical guidewire. Many parts of catheter 50 are conventional, and there are substitutes known to those skilled in the art. Helix wire 60 slidably passes through inner lumen 57.

An outer plastic skin 80 is attached. Balloon 82 is mounted on skin 80 in a conventional manner so that the interior balloon is open to outer lumen 59 for inflation. In this embodiment, the wire 60 operates to provide a torque transmitting body which is pushable while remaining flexible. Torque is transmitted by rotating handle 51.

FIG. 5 illustrates another junction structure usable in guidewires such as that shown in FIG. 1. Shaft 90 includes a narrowed distal end 92, which may be formed by grinding. A sleeve 94 is mounted over narrowed distal section 92. Tip coil 98 is mounted over helix 96 and both coil 98 and helix 96 are attached to sleeve 94

In FIG. 6, another attachment mode is illustrated wherein shaft 100 is a hollow tube with a lumen 102. Helix wire 104 is mounted within lumen 102 and brazed to shaft 100. Tip spring 106 is mounted over helix 104 and is brazed to shaft 100.

FIG. 7 illustrates an alternative embodiment which a guidewire 110 includes a main shaft 112 constructed entirely of a helically twisted flat wire. No solid or tubular shaft is used as in the other illustrated embodiments. Shaft 112 is tapered, in this example, at 114. A tip spring 116 is mounted over the tapered section of shaft 112 and brazed to shaft 112. In the particular illustrated embodiment, tip spring 116 has a proximal end 118 which is generally adjacent to the beginning of the taper at 114. A distal end 120 of tip spring 116 is attached, such as by brazing, to metallic tip 122. The tapered section of shaft 112 has attached to its distal end a ribbon wire 114 which is attached, such as by brazing, to tip 122. Proximal shaft section 112 may be coated with plastic jacket 232 up to area 114 at the spring coil section, although in certain embodiments it will not be coated. In this embodiment, the torque transmitting characteristics of the helical wire are used for the entire guidewire.

An alternate embodiment of the tip area is illustrated in FIG. 7a where distal end 120 of wire 104 is attached directly to tip 122. Distal end 120 may be tapered to round diameter.

Another embodiment of the present invention is illustrated in FIG. 8 in which a full length helical wire 130 is employed. Helical wire 130 is constructed as discussed above and tapered in the manner similar to helical shaft 112 of FIG. 7. Helical wire 130 has a generally cylindrical proximal section 132, a tapered section 134 and a flat, narrow tip 135. No tip spring is used in this embodiment. All of helical wire 130 is encased in a polymer jacket 136. Tip flexibility is provided in that tapered section 134 and flattened tip 135 will flex along with the encasing jacket 136. Jacket 136 has thickness selected for the desired flexibility. In the illustrated embodiment, jacket 136 is only thick enough to cover section 132. Jacket 136 tapers along section 134 and tip 135 to provide graduated flexibility.

No tip or spring is needed to provide guidability through the arteries. In this embodiment, shaft 130 provides both pushability and torque transmitting characteristics desirable in a guidewire. Additionally, it is very flexible in a transverse direction.

Turning to FIG. 9a, the basic construction of a unitary guidewire of the present invention is shown. In this embodiment, the entire guidewire is unitary, i.e., formed of a single piece of material (with the exception of the tip coil). Such construction may avoid weak spots or reduced torque transmission due to uncentered junctures. Unitary guidewire 210 includes a shaft 212 formed adjacent to tapering region 214 which is adjacent to flat band 218 having a helical section 226. Distal to helical wire 226 is a flat distal section 228 of band 218. Distal section 228 is stepped up in area 225 to form a distal portion 230 of the guidewire. Shaft 212, tapering region 214 and distal portion 230 are cylindrical in cross-section.

As shown in FIG. 9b, the device can terminate in a tip member 232 having the same diameter as shaft 212, just distal to a smaller diameter distal section 230. Spring coil 229, formed of a radiopaque material such as platinum, is brazed or welded to the circumference of distal portion 230. Spring coil 227, formed of stainless steel is brazed to tapered portion 214 immediately adjacent shaft 212 and surrounds helical section 226. The two coils are interwound and brazed to helical section 226 at a point near the distal end of the helix. Tip coil 229 provides radiopacity, and tip coil 227 promotes torquability without hindrance by protecting helical section 226 from the vessel wall, because the wire itself twists within coil 227 rather than encountering the vessel wall.

The actual construction of the wire 210 can be seen in FIG. 10 which depicts a side elevation of a unitary guidewire of the present invention before the helical twisting of the wire has occurred. Guidewire 210 is designed so that the distal portion and the shaft 212 are both cylindrical in cross-section. Tapering region 214, also cylindrical in cross-section, is tapered at a constant rate from 215 to 220 then flattened to retain a width of about 0.008 inch along its length. 215 to 219 is formed to a helical coil leaving approximately one cm of a flat section from 219 to 220. The coil spring 227 is then assembled by brazing the proximal end of the coil spring 227 to the 214 tapered section, and the distal end of coil spring 229 is welded to the 230 cylindrical end. The distal end of coil spring 227 is brazed to the proximal end of coil spring 229.

To use the guidewire for insertion of a catheter, a guiding catheter is normally threaded through the vascular system to a position near the coronary veins or arteries. The tip of the guidewire is then usually bent or deflected to promote steerability. The guidewire is inserted through the guiding catheter and steered and further inserted into the twisting pathways of the coronary arteries, to the point of interest, usually through a stenosis to be reduced.

While the invention disclosed in terms of particularly illustrated embodiments, it is understood that those skilled in the art may use in the invention in other forms. The preceding specific embodiments are illustrative of the practice of the invention. Other expedients known to those skilled in the art or disclosed herein, may be employed without departing from the spirit of the invention or the scope of the appended claims.

We claim:

1. A torque transmitting medical guidewire comprising:
   a shaft with a distal end and a proximal end;
   a helical wire having a proximal end and a distal end constructed from a generally flat, rectangular member having an edge, twisted around the wire's longitudinal axis so that the edge forms a helix such that torque applied to the wire at the proximal end is transmitted to the distal end, the proximal end of the helical wire being fixedly mounted to the distal end of the shaft;
   a means for rotating the helical wire; and
   a coil surrounding the helical wire, the coil having a distal end and a proximal end, the proximal end of the coil being fixedly mounted near the distal end of the shaft proximal to the helical wire.

2. A guidewire according to claim 1 wherein the helical wire is approximately 0.03 inches thick and approximately 0.01 inches wide.

3. A torque-transmitting medical guidewire comprising:
   a shaft with a distal end and a proximal end;
   a helical wire having a proximal end and a distal end constructed from a generally flat, rectangular member having an edge, twisted around the wire's longitudinal axis so that the edge forms a helix such that torque applied to the wire at the proximal end is transmitted to the distal end, the proximal end of the helical wire being fixedly mounted to the distal end of the shaft; and
   a coil surrounding the helical wire, the coil having a distal end and a proximal end, the proximal end of the coil being fixedly mounted near the distal end of the shaft proximal to the helical wire.

4. A guidewire according to claim 3 wherein the helical wire is approximately 0.03 inches thick and approximately 0.010 inches wide.

5. A guidewire according to claim 3 wherein the helical wire is formed of a biocompatible metal.

6. A guidewire according to claim 1 or 3 wherein the proximal end of the helical wire is straight.

7. A guidewire according to claim 1 or 3 wherein the distal end of the shaft is of reduced diameter, and the coil is mounted on the shaft in the area of the reduced diameter.

8. A guidewire according to claim 1 or 3 wherein the distal end of the helical wire is straight.

9. A guidewire according to claim 8 with a tip wire having a proximal end and a distal end, the proximal end of the tip wire being fixedly attached to the straight portion at the distal end of the helical wire.

10. A guidewire according to claim 9 wherein a tip member is fixedly mounted to the distal end of the tip wire.

11. A guidewire according to claim 8 wherein a tip member is fixedly mounted to the distal end of the helical wire.

12. A guidewire according to claim 10 wherein the distal end of the coil is fixedly mounted to the tip member.

13. A guidewire according to claim 11 wherein the distal end of the coil is fixedly mounted to the tip member.

14. A guidewire according to claim 6 wherein the shaft is constructed of a hollow tube, the hollow tube having a proximal section of a first diameter and a distal portion of a small diameter with the straight proximal end of the helical wire being fixedly attached to the shaft portion of smaller diameter and the proximal end of the coil being fixedly mounted over the straight proximal end of the helical wire.

15. A guidewire according to claim 6 wherein
the shaft is hollow and has a proximal section of a first diameter and a distal portion of a smaller diameter with the straight proximal end of the helical wire being fixedly attached to the shaft portion of smaller diameter and the proximal end of the coil being fixedly mounted over the distal shaft portion;
a balloon is mounted over at least a portion of the helical wire; and
a plastic sheath connected between the shaft and balloon encases the coil defining a lumen which is in fluid communication with the balloon.

16. A torque-transmitting medical apparatus comprising:
a helical wire having a proximal end and a distal end constructed from a generally flat, rectangular member having an edge, twisted around the wire's longitudinal axis so that the edge forms a helix such that torque applied to the wire at the proximal end is transmitted tot he distal end, the distal end of the helical wire having a flat section;
a coil surrounding the helical wire, the coil having a distal end and a proximal end, the proximal end of the coil being fixedly mounted to the proximal end of the helical wire;
a plastic sheath encasing the coil and defining a lumen which is in fluid communication with a balloon;
the balloon mounted to the sheath near the distal end of the helical wire; and
a round tip member fixedly attached to the distal end of the helical wire with the distal end of the coil being fixedly mounted to the tip member.

17. A torque-transmitting medical guidewire comprising:
a shaft with a distal end and a proximal end, the shaft having a narrowed distal end;
a sleeve mounted over the narrowed distal end of the shaft;
a helical wire having a proximal end and a distal end constructed from a generally flat, rectangular member having an edge, twisted around the wire's longitudinal axis so that the edge forms a helix such that torque applied to the wire at the proximal end is transmitted to the distal end, the proximal end of the helical wire being fixedly mounted to the sleeve; and
a coil surrounding the helical wire, the coil having a distal end and a proximal end, the proximal end of the coil being fixedly mounted to the sleeve.

18. A torque-transmitting medical guidewire comprising:
a shaft comprised of hollow tube with a distal end and a proximal end and having a lumen therethrough;
a helical wire having a proximal end and a distal end, the helical wire constructed from a generally flat, rectangular member having an edge, twisted around the wire's longitudinal axis so that the edge forms a helix such that torque applied to the wire at the proximal end is transmitted to the distal end, the proximal end of the helical wire being fixedly mounted within the lumen of the shaft; and
a coil surrounding the helical wire, the coil having a distal end and a proximal end, the proximal end of the coil being fixedly mounted to the shaft.

19. A torque-transmitting medical guidewire comprising:
a helical wire having a proximal end and a distal end constructed from a generally flat, rectangular member having an edge, twisted around the wire's longitudinal axis so that the edge from a helix such that torque applied to the wire at the proximal end is transmitted to the distal end, wherein the distal end of the helical wire is straight; and
a coil surrounding the helical wire, the coil having a distal end and a proximal end, the proximal end of the coil being fixedly mounted to a tapered area of smaller diameter than a proximal section of the helical wire.

20. A guidewire according to claim 19 wherein the proximal section of the helical wire is coated with a plastic jacket up to the tapered area.

21. A guidewire according to claim 19 wherein a rounded tip member is fixedly attached to the distal end of the helical wire with the distal end of the coil being fixedly mounted to the tip member.

22. A guidewire according to claim 19 further comprising:
a tip wire having a proximal end and a distal end, the proximal end of the tip wire being fixedly mounted to the straight portion at the distal end of the helical wire; and
a rounded tip member fixedly attached to the distal end of the tip wire with the distal end of the coil being fixedly mounted to the tip member.

23. A torque-transmitting medical guidewire comprising:
a helical wire a proximal end and a distal end the helical wire being constructed from a generally flat, rectangular member having an edge, twisted around the wire's longitudinal axis so that the edge forms a helix such that torque applied to the wire at the proximal end is transmitted to the distal end, wherein the distal end of the helical wire is straight and tapers into an area of greater diameter forming a unitary tip member, and wherein the proximal end of the helical wire tapers outwardly into a larger straight diameter forming a unitary shaft; and
a coil surrounding the helical wire, the coil having a distal end and a proximal end, the proximal end of the coil being fixedly mounted to the unitary shaft and the distal end of the coil being mounted to the unitary tip member.

* * * * *

UNITED STATES PATENT AND TRADEMARK OFFICE
CERTIFICATE OF CORRECTION

PATENT NO. : 5,313,967
DATED : May 24, 1994
INVENTOR(S) : Glen L. Lieber et al.

It is certified that error appears in the above-indentified patent and that said Letters Patent is hereby corrected as shown below:

Column 4, line 67 of the patent, "114" should be --124--.

Column 6, line 41 of the patent, "0.03" should be --0.003--.

Column 6, line 59 of the patent, "0.03" should be --0.003--.

Column 7, line 44 of the patent, "tot he" should be --to the--.

Signed and Sealed this

Thirteenth Day of September, 1994

Attest:

BRUCE LEHMAN

Attesting Officer

Commissioner of Patents and Trademarks